US 010117716B2

(12) United States Patent
Ogawa et al.

(10) Patent No.: US 10,117,716 B2
(45) Date of Patent: Nov. 6, 2018

(54) MEDICAL MANIPULATOR SYSTEM

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/375,374

(22) Filed: Dec. 12, 2016

(65) Prior Publication Data

US 2017/0151028 A1 Jun. 1, 2017

Related U.S. Application Data

(63) Continuation of application No. PCT/JP2015/078063, filed on Oct. 2, 2015.

(Continued)

(51) Int. Cl.
*A61B 17/00* (2006.01)
*A61B 46/10* (2016.01)
(Continued)

(52) U.S. Cl.
CPC ........ *A61B 46/10* (2016.02); *A61B 17/00234* (2013.01); *A61B 17/29* (2013.01);
(Continued)

(58) Field of Classification Search
None
See application file for complete search history.

(56) References Cited

U.S. PATENT DOCUMENTS 5,386,816 A   2/1995 Inoue et al.
6,331,181 B1  12/2001 Tierney et al.
(Continued)

FOREIGN PATENT DOCUMENTS

EP   2 324 789 A1   5/2011
EP   2 891 449 A1   7/2015
(Continued)

OTHER PUBLICATIONS

International Search Report dated Dec. 22, 2015 issued in International Application No. PCT/JP2015/078063.
(Continued)

*Primary Examiner* — Richard Louis
(74) *Attorney, Agent, or Firm* — Scully, Scott, Murphy & Presser, P.C.

(57) ABSTRACT

A medical manipulator system including: a manipulator provided with an elongated portion, a movable portion which has one or more joints, and a driving portion which is disposed at a proximal end of the elongated portion and which drives the movable portion; a medical device having a channel that can accommodate at least a portion of the elongated portion and the movable portion; a manipulation input portion that generates an operation instruction for moving the manipulator between a treatment state in which the movable portion protrudes from a distal end of the channel and an accommodated state in which the movable portion is accommodated in the channel in accordance with a manipulation instruction input; and a notifying portion that notifies a situation in which the manipulator is shifting from the treatment state to the accommodated state.

8 Claims, 11 Drawing Sheets

Related U.S. Application Data

(60) Provisional application No. 62/168,987, filed on Jun. 1, 2015.

(51) Int. Cl.

| | | |
|---|---|---|
| *A61B 34/32* | (2016.01) | |
| *A61B 34/37* | (2016.01) | |
| *A61B 34/00* | (2016.01) | |
| *A61B 90/00* | (2016.01) | |
| *A61B 17/29* | (2006.01) | |
| *B25J 3/00* | (2006.01) | |
| *B25J 13/02* | (2006.01) | |
| *A61B 18/14* | (2006.01) | |
| *A61B 90/50* | (2016.01) | |
| *A61B 17/34* | (2006.01) | |
| *A61B 34/30* | (2016.01) | |
| *B32B 3/26* | (2006.01) | |
| *A61B 18/00* | (2006.01) | |

(52) U.S. Cl.
CPC ...... *A61B 17/3423* (2013.01); *A61B 18/1492* (2013.01); *A61B 34/30* (2016.02); *A61B 34/32* (2016.02); *A61B 34/37* (2016.02); *A61B 34/70* (2016.02); *A61B 34/71* (2016.02); *A61B 34/74* (2016.02); *A61B 90/03* (2016.02); *A61B 90/06* (2016.02); *A61B 90/50* (2016.02); *B25J 3/00* (2013.01); *B25J 13/02* (2013.01); *A61B 18/1482* (2013.01); *A61B 2017/00314* (2013.01); *A61B 2017/00323* (2013.01); *A61B 2017/00477* (2013.01); *A61B 2017/00929* (2013.01); *A61B 2018/00077* (2013.01); *A61B 2018/00083* (2013.01); *A61B 2018/1412* (2013.01); *A61B 2034/301* (2016.02); *A61B 2034/302* (2016.02); *A61B 2034/306* (2016.02); *A61B 2090/034* (2016.02); *B32B 3/266* (2013.01); *H05K 999/99* (2013.01)

(56) References Cited

U.S. PATENT DOCUMENTS

| | | | |
|---|---|---|---|
| 7,972,298 | B2 | 7/2011 | Wallace et al. |
| 8,638,057 | B2 | 1/2014 | Goldberg et al. |
| 8,720,448 | B2 | 5/2014 | Reis et al. |
| 2002/0128649 | A1 | 9/2002 | Bacher et al. |
| 2004/0019352 | A1 | 1/2004 | Kidooka |
| 2005/0075739 | A1 | 4/2005 | Nishizawa |
| 2005/0096502 | A1* | 5/2005 | Khalili .......... A61B 1/018 600/106 |
| 2005/0154439 | A1 | 7/2005 | Gunderson |
| 2005/0222495 | A1 | 10/2005 | Okada et al. |
| 2005/0272975 | A1 | 12/2005 | McWeeney et al. |
| 2006/0282063 | A1 | 12/2006 | Gotani |
| 2007/0163597 | A1 | 7/2007 | Mikkaichi et al. |
| 2008/0108443 | A1 | 5/2008 | Jinno et al. |
| 2008/0193260 | A1 | 8/2008 | Yokokohji et al. |
| 2008/0281155 | A1 | 11/2008 | Fujikura |
| 2008/0294004 | A1 | 11/2008 | Fujikura |
| 2009/0018390 | A1 | 1/2009 | Honda et al. |
| 2009/0105726 | A1 | 4/2009 | Sugiyama |
| 2009/0182200 | A1 | 7/2009 | Golden et al. |
| 2009/0248039 | A1 | 10/2009 | Cooper et al. |
| 2009/0275798 | A1 | 11/2009 | Naito |
| 2010/0030023 | A1 | 2/2010 | Yoshie |
| 2010/0170519 | A1 | 7/2010 | Romo et al. |
| 2010/0298646 | A1 | 11/2010 | Stellon et al. |
| 2010/0318100 | A1* | 12/2010 | Okamoto ......... A61B 1/0052 606/130 |
| 2010/0331856 | A1 | 12/2010 | Carlson et al. |
| 2011/0168189 | A1 | 7/2011 | Cooper et al. |
| 2012/0271102 | A1* | 10/2012 | Katayama ........ A61B 1/00009 600/104 |
| 2012/0289973 | A1 | 11/2012 | Prisco et al. |
| 2013/0331857 | A9 | 12/2013 | Prisco et al. |
| 2014/0166023 | A1 | 6/2014 | Kishi |
| 2014/0296771 | A1 | 10/2014 | Naito |
| 2015/0238180 | A1 | 8/2015 | Weitzner et al. |

FOREIGN PATENT DOCUMENTS

| | | |
|---|---|---|
| JP | S62-72091 U | 5/1987 |
| JP | H05-095893 A | 4/1993 |
| JP | H07-095953 A | 4/1995 |
| JP | H10-276965 A | 10/1998 |
| JP | 2004-344180 A | 12/2004 |
| JP | 2005-103741 A | 4/2005 |
| JP | 2005-287963 A | 10/2005 |
| JP | 2006-334695 A | 12/2006 |
| JP | 2007-167644 A | 7/2007 |
| JP | 2007-517597 A | 7/2007 |
| JP | 2007-307289 A | 11/2007 |
| JP | 2007-530155 A | 11/2007 |
| JP | 2008-114339 A | 5/2008 |
| JP | 2008-278968 A | 11/2008 |
| JP | 2009-011809 A | 1/2009 |
| JP | 2009-100873 A | 5/2009 |
| JP | 2009-523032 A | 6/2009 |
| JP | 2009-240657 A | 10/2009 |
| JP | 2009-268592 A | 11/2009 |
| JP | 2010-035768 A | 2/2010 |
| JP | 4420593 B | 2/2010 |
| JP | 2010-525838 A | 7/2010 |
| JP | 4420593 B | 12/2010 |
| JP | 2011-509718 A | 3/2011 |
| JP | 2011-072570 A | 4/2011 |
| JP | 2011-072574 A | 4/2011 |
| JP | 2012-070953 A | 4/2012 |
| JP | 2012-152562 A | 8/2012 |
| JP | 2013-034833 A | 2/2013 |
| JP | 2014-028291 A | 2/2014 |
| JP | 2014-111080 A | 6/2014 |
| JP | 2014-521375 A | 8/2014 |
| JP | 2015-006423 A | 1/2015 |
| WO | WO 1997/029690 A1 | 8/1997 |
| WO | WO 1998/025666 A1 | 6/1998 |
| WO | WO 2005/070339 A1 | 8/2005 |
| WO | WO 2005/094665 A2 | 10/2005 |
| WO | WO 1997/029690 A1 | 4/2007 |
| WO | WO 2007/041093 A1 | 4/2007 |
| WO | WO 2007/070693 A2 | 6/2007 |
| WO | WO 2009/037576 A2 | 3/2009 |
| WO | WO 2009/091836 A1 | 7/2009 |
| WO | WO 2010/055745 A1 | 5/2010 |
| WO | WO 2012/158449 A1 | 11/2012 |
| WO | WO 2013/018927 A1 | 2/2013 |
| WO | 2014/034532 A1 | 3/2014 |

OTHER PUBLICATIONS

International Search Report dated Nov. 10, 2015 issued in International Application No. PCT/JP2015/074792.

International Search Report dated Jan. 26, 2016 issued in International Application No. PCT/JP2015/082622.

International Search Report dated Jan. 12, 2016 issued in International Application No. PCT/JP2015/082118.

International Search Report dated Jun. 28, 2016 issued in International Application No. PCT/JP2015/063786.

International Search Report dated Jun. 28, 2016 issued in International Application No. PCT/JP2016/063786.

Office Action dated Apr. 19, 2018 received in U.S. Appl. No. 15/804,068.

Office Action dated Apr. 19, 2018 received in U.S. Appl. No. 15/819,045.

Office Action dated Jun. 8, 2018 received in U.S. Appl. No. 15/824,481.

* cited by examiner

ABSTRACT
MEDICAL MANIPULATOR SYSTEM

CROSS-REFERENCE TO RELATED APPLICATIONS

This application is a Continuation application of International Application No. PCT/JP2015/078063 filed on Oct. 2, 2015, which claims priority to Provisional Application No. 62/168,987 filed on Jun. 1, 2015. The Contents of International Application No. PCT/JP2015/078063 and Provisional application No. 62/168,987 are hereby incorporated herein by reference in their entirety.

TECHNICAL FIELD

The present invention relates to a medical manipulator system.

BACKGROUND ART

There is a known medical manipulator system that employs a master-slave system and with which treatment is performed by making a multijoint treatment tool protrude from the distal end of a channel of an endoscope. (For example, see Patent Literature 1.)

In addition, there is a known medical manipulator system which employs a master-slave system, which is provided with a master-side manipulation portion including a handle that an operator grips in the palm and an armrest on which the arm of the hand gripping the handle is placed, with which the position of a slave-side manipulator is moved by moving the armrest, and with which the orientation of the manipulator is changed by manipulating the handle. (For example, see Patent Literature 2.)

CITATION LIST

Patent Literature

{Patent Literature 1} Japanese Unexamined Patent Application, Publication No. 2009-100873
{Patent Literature 2} Japanese Unexamined Patent Application, Publication No. 2005-103741

SUMMARY OF INVENTION

An aspect of the present invention is a medical manipulator system including: a manipulator that is provided with an elongated portion, a movable portion which has one or more joints and which is disposed at a distal end of the elongated portion, and a driving portion which is disposed at a proximal end of the elongated portion and which drives the movable portion; a medical device having a channel that can accommodate at least a portion of the elongated portion and the movable portion so as to be movable in a longitudinal direction; a manipulation input portion that generates an operation instruction for moving the manipulator in a longitudinal direction of the elongated portion between a treatment state in which the movable portion completely protrudes from a distal end of the channel and an accommodated state in which the movable portion is accommodated in the channel in accordance with a manipulation instruction input by an operator; and a notifying portion that notifies a situation in which the movable portion is shifting from the treatment state to the accommodated state.

DESCRIPTION OF EMBODIMENT

A medical manipulator system 1 according to an embodiment of the present invention will be described below with reference to the drawings.

Figure 1:
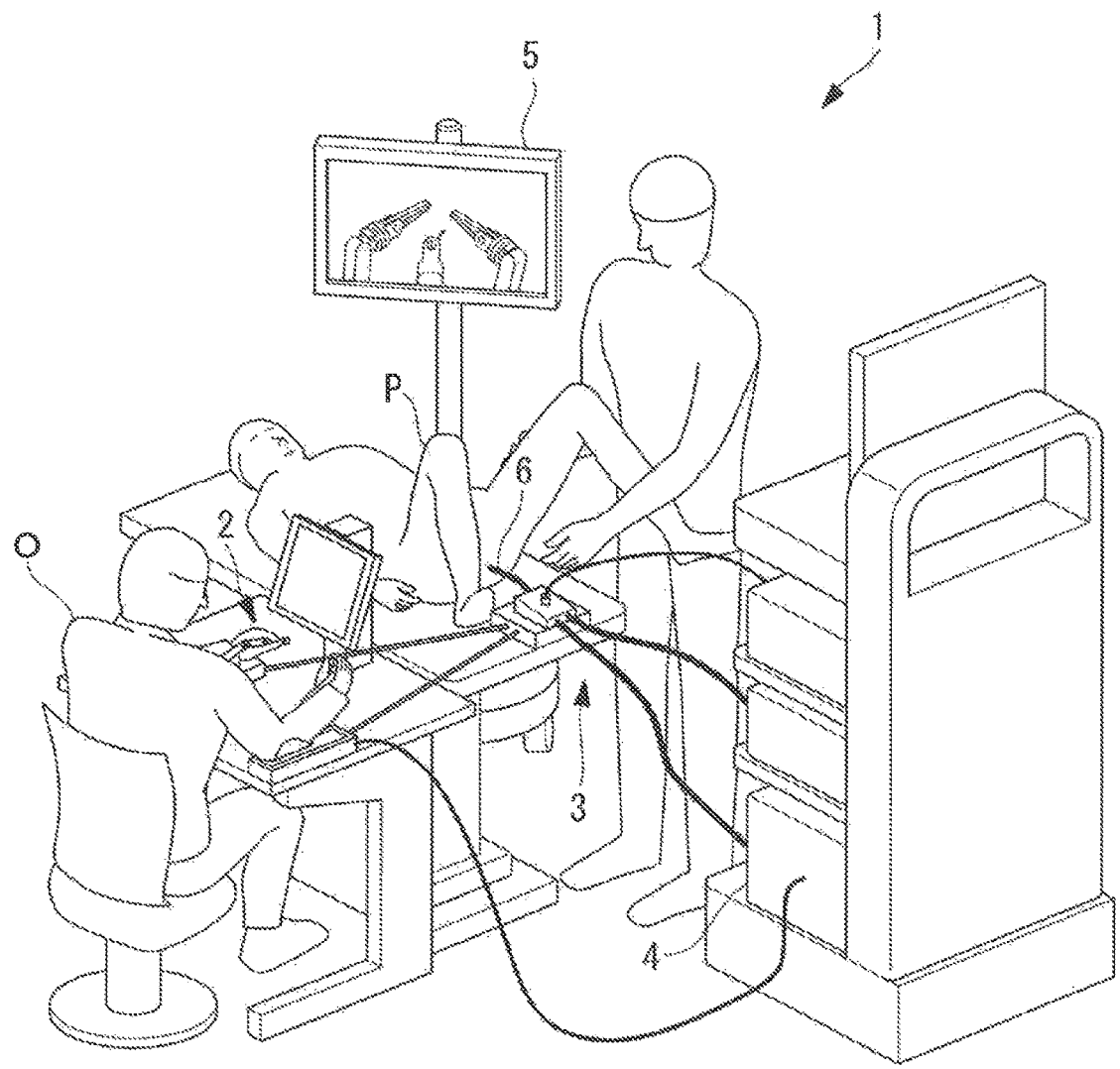
FIG. 1 is an overall configuration diagram showing a medical manipulator system according to an embodiment of the present invention.
Figure 2:
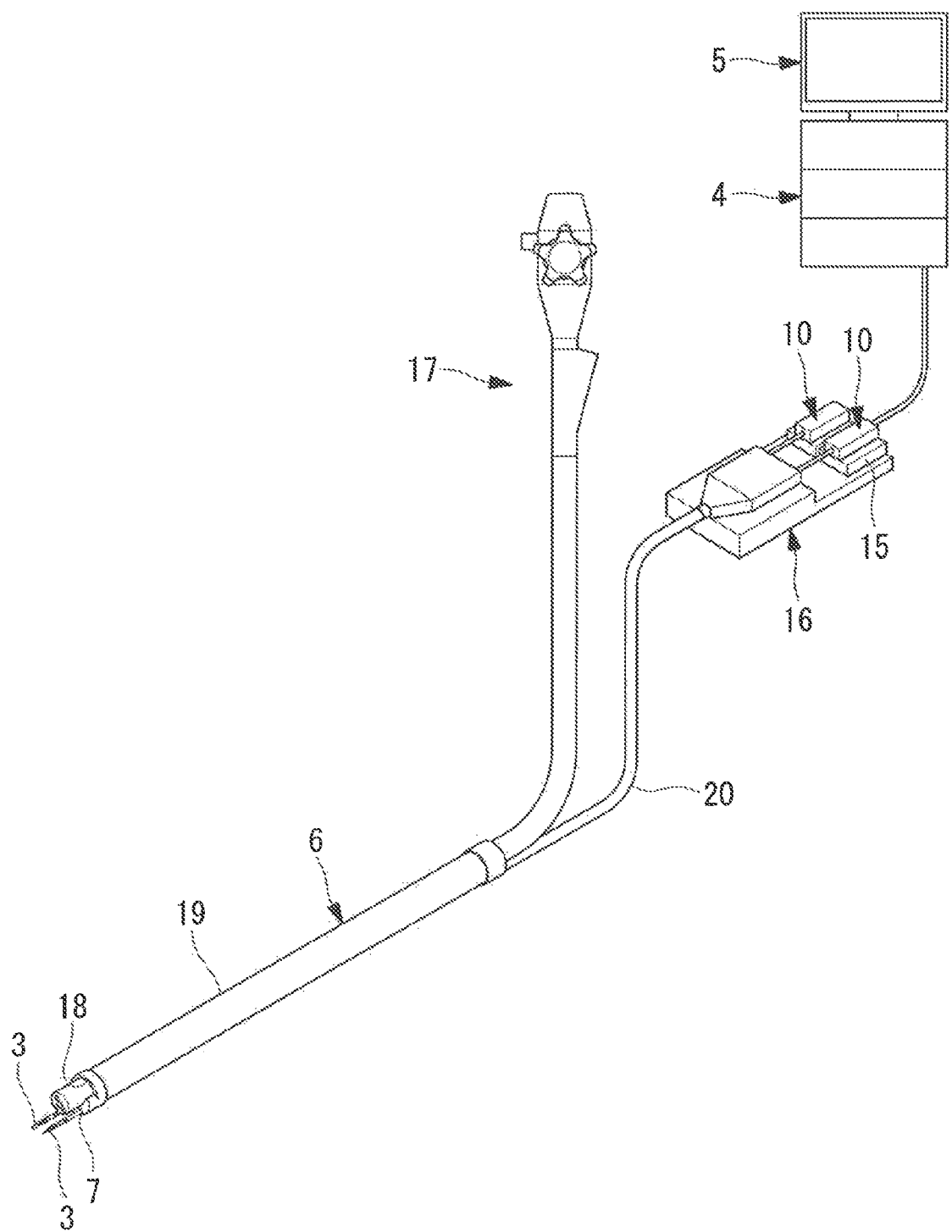
FIG. 2 is a perspective view showing a portion of the medical manipulator system in FIG. 1.

As shown in FIGS. 1 and 2, the medical manipulator system 1 according to this embodiment is provided with: manipulation input portions 2 that are manipulated by an operator O; an overtube (medical device) 6 that is inserted into the body cavity of a patient P; two manipulators 3 that are individually inserted into two channels 7 in the overtube 6; a controller 4 that controls the manipulators 3 on the basis of manipulation of the manipulation input portions 2; and a monitor 5.

Figure 3:
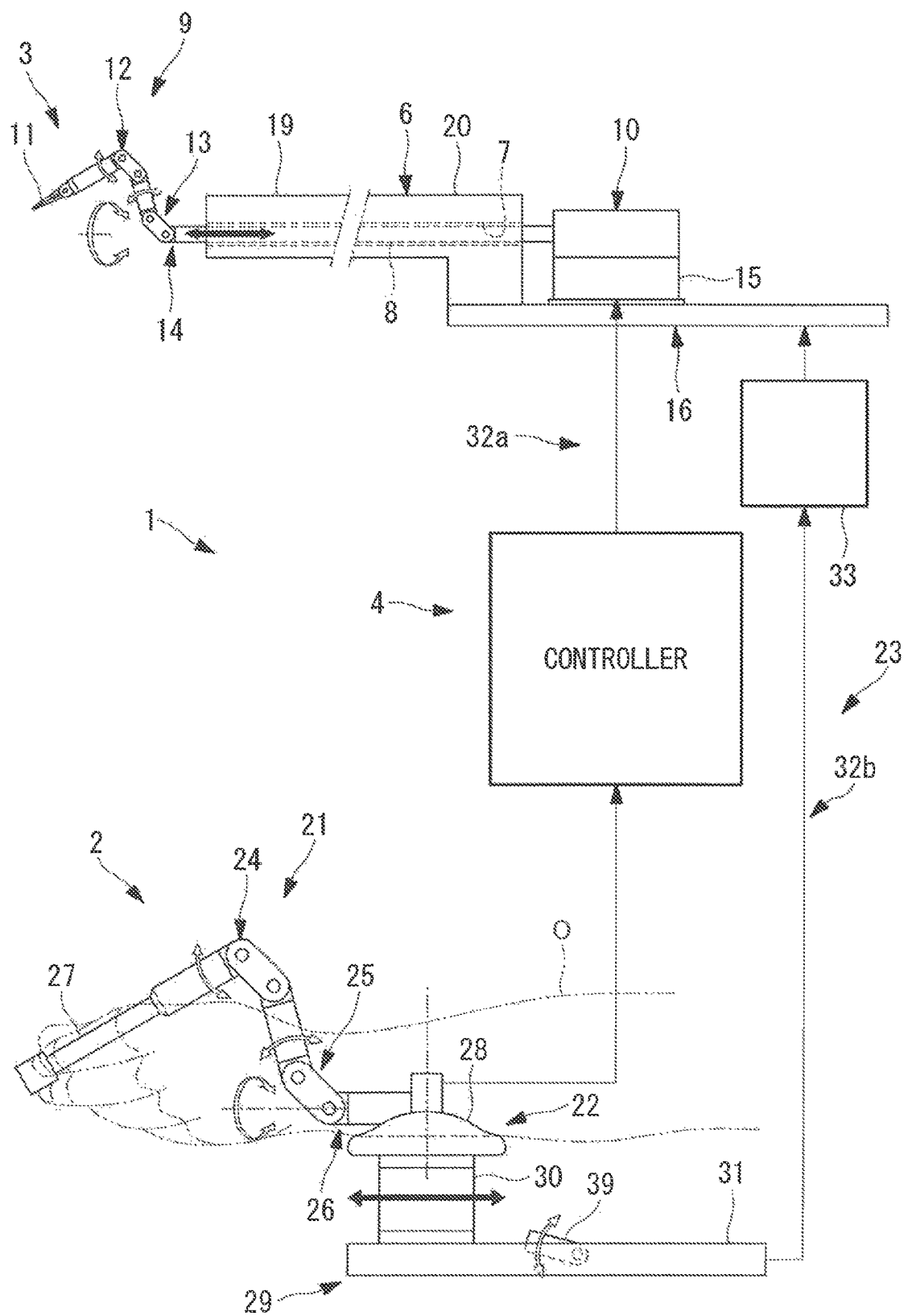
FIG. 3 is a diagram showing a manipulator, a manipulation input portion, and a controller that are employed in the medical manipulator system in FIG. 1.

As shown in FIG. 3, the manipulators 3 are provided with: inserted portions (elongated portions) 8 that are inserted into the body of the patient P via the channels 7 in the overtube 6 which will be described later; movable portions 9 that are provided at distal ends of the inserted portions 8; and driving portions 10 that are disposed on the proximal-end side of the inserted portions 8 and that drive the movable portions 9 by means of driving-power transmitting members (not shown), such as wires or the like.

The movable portions 9 are provided with: treatment portions 11 that are disposed at the most distal ends and that treat an affected site in the body by acting thereon; and a plurality of joints 12, 13, and 14 that change the positions and orientations of the distal ends of the treatment portions 11. The treatment portions 11 are, for example, gripping forceps, high-frequency knives, or the like.

In addition, as shown in FIG. 3, the manipulators 3 are detachably connected to the individual driving portions 10, and are provided with a motor unit 15 that has a built-in electric driving source (not shown), such as a motor or the like, which gives driving powers to each of the driving portions 10, and an advancing/retracting mechanism 16 that moves the motor unit 15 along a straight path.

As shown in FIGS. 2 and 3, the overtube 6 is a tube formed of a material having flexibility and is provided with: a distal-end-side tube-like portion 19 having the two manipulator channels (channels) 7 through which the manipulators 3 are individually made to pass and a single endoscope channel 18 through which an endoscope 17 is made to pass; and a base-end-side tube-like portion 20 that extends from the base end of the distal-end-side tube-like portion 19 so as to extend the two manipulator channels 7 toward the base-end side.

As shown in FIG. 3, the manipulation input portions 2 are provided with: first manipulation portions 21 that the operator O grips with his/her hands; second manipulation portions 22 that the operator O manipulates with the wrists of his/her arms; and instruction transmitting portions 23 that transmit manipulation instructions input via these manipulation portions 21 and 22 to the manipulators 3.

The first manipulation portions 21 are formed in a shape that is similar to that of the movable portions 9 of the manipulators 3, and are configured so that distal-end portions 27 supported by joints 24, 25, and 26, which are provided in the same number as those of the movable portions 9, are gripped by the hand of the operator O and are moved by his/her palm or fingers. The first manipulation portions 21 are provided with sensors (not shown) that detect angles of the individual joints 24, 25, and 26 constituting the first manipulation portions 21.

The sensors are configured so as to generate electrical signals in accordance with the angles of the individual joints 24, 25, and 26. By doing so, the individual first manipulation portions 21 are configured so that the operator O can input manipulation instructions by using his/her palm or fingers, and thus, operation instructions can be generated in the form of electrical signals.

The second manipulation portions 22 are provided with armrests 28 that are secured to the proximal portions of the first manipulation portions 21 and linear motion mechanisms 29 that support the armrests 28 and the first manipulation portions 21 in an integrally movable manner. The armrests 28 are disposed at positions at which portions of the arms close to the wrists of the hands gripping the distal-end portions 27 are placed when the operator O grips the distal-end portions 27 of the first manipulation portions 21.

Figure 4:
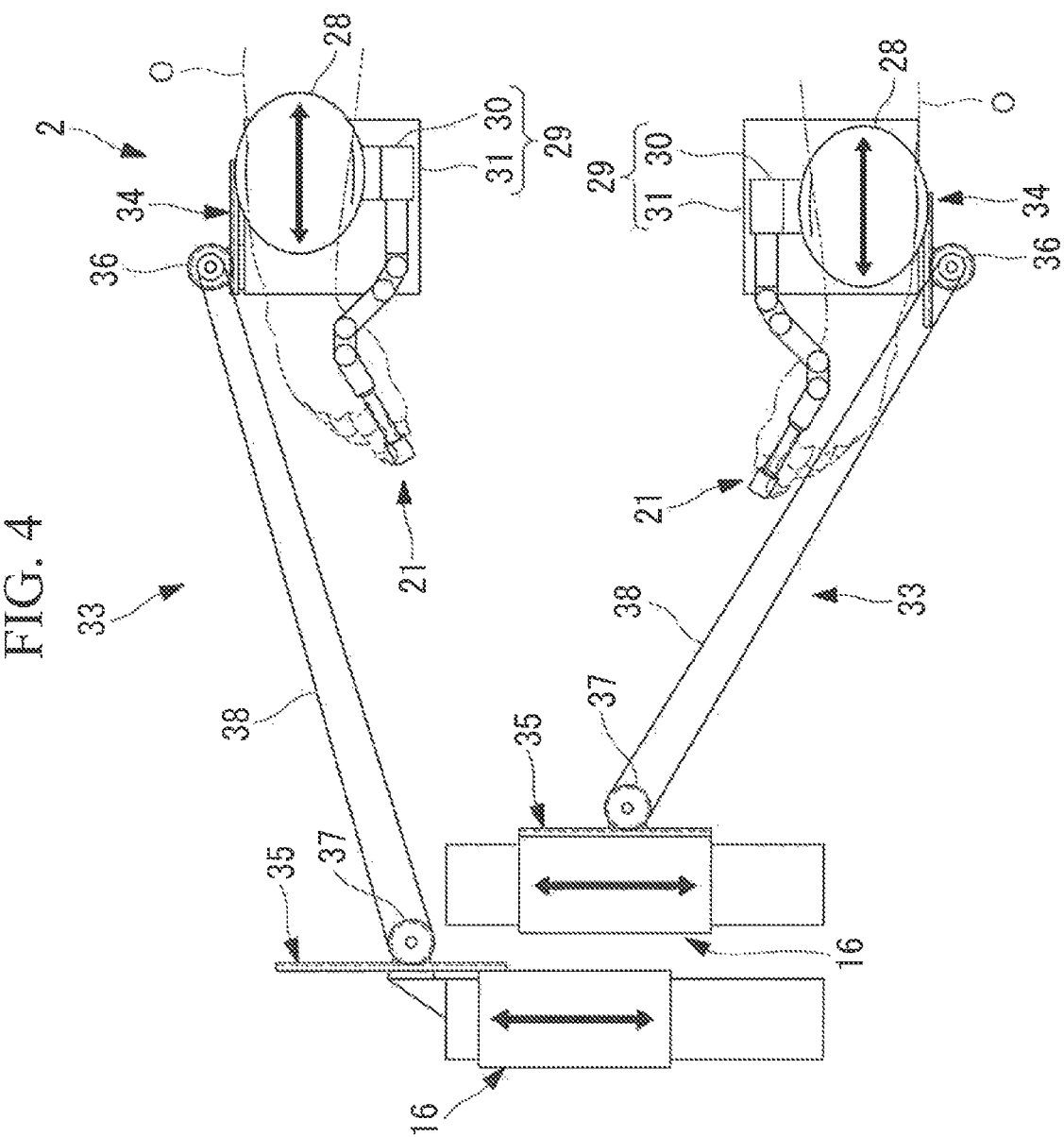
FIG. 4 is a plan view for explaining a second manipulation portion, an instruction transmitting portion, and an advancing/retracting mechanism of the manipulation input portion of the medical manipulator system in FIG. 1.

The linear motion mechanisms 29 are provided with sliders 30 on which the armrests 28 and the first manipulation portions 21 are secured, and linear guides 31 that support the sliders 30 so as to be movable in a horizontal direction, as indicated by the filled arrows in FIGS. 3 and 4. By moving the sliders 30 in the horizontal direction by means of the arms placed on the armrests 28, the positions of the first manipulation portions 21 can be moved while maintaining the state in which the first manipulation portions 21 are gripped. By doing so, the second manipulation portions 22 are configured so that the operator O can input manipulation instructions by using his/her wrists or arms, and thus, operation instructions can be generated by the forces input by means of the wrists or the arms, which serve as mechanical driving forces for each of the two sliders 30. Note that, in addition to the case in which the operation instructions are generated in the form of the mechanical driving forces generated by the sliders 30, a system in which the operation instructions are generated in the form of electrical driving forces may be employed.

The instruction transmitting portions 23 are provided with electrical-signal transmitting portions 32*a* that connect the first manipulation portions 21 and the motor unit 15, and mechanical-driving-power transmitting portions 32*b* that connect the second manipulation portions 22 and the advancing/retracting mechanisms 16.

The electrical-signal transmitting portions 32*a* transmit the operation instructions generated by the first manipulation portions 21 in the form of electrical signals to the controller 4, and provide the individual motors of the motor unit 15 with the instruction signals generated by the controller 4. The controller 4 is configured so as to control the individual motors by calculating the amount of rotational movement and the rotational speed of the individual motors of the motor unit 15 on the basis of the operation instructions generated by the first manipulation portions 21.

As shown in FIG. 3, the mechanical-driving-power transmitting portions 32*b* are provided with transmission portions 33 that convert the linear motions moving forward and backward the sliders 30 of the manipulation input portions 2 into the linear motions of the advancing/retracting mechanism 16.

As shown in FIG. 4, the transmission portions 33 are provided with: first rack-and-pinion mechanisms 34 that convert the amounts of straight movement of the sliders 30 of the manipulation input portions 2 into the rotational angles; second rack-and-pinion mechanisms 35 that convert the rotational motions into the amount of straight movements of the advancing/retracting mechanisms 16; pulleys 36 and 37 that are secured to pinion gears of these rack-and-pinion mechanisms 34 and 35, respectively; and belts 38 that are wound around these pulleys 36 and 37.

In this embodiment, the motion range of the sliders 30 of the linear motion mechanisms 29 corresponds to the motion range of the advancing/retracting mechanisms 16 that moves the manipulators 3 in the longitudinal direction of the inserted portions 8 relative to the overtube 6. In other words, when the sliders 30 are moved between the most front-end position and the most rear-end position, the manipulators 3 can be moved between a treatment state in which the entire movable portions 9 provided at the distal ends of the manipulators 3 protrude forward from the manipulator channels 7 of the overtube 6, as shown in FIG. 5, and an accommodated state in which the entire movable portions 9 are accommodated in the manipulator channels 7 of the overtube 6, as shown in FIG. 6.

Figure 5:
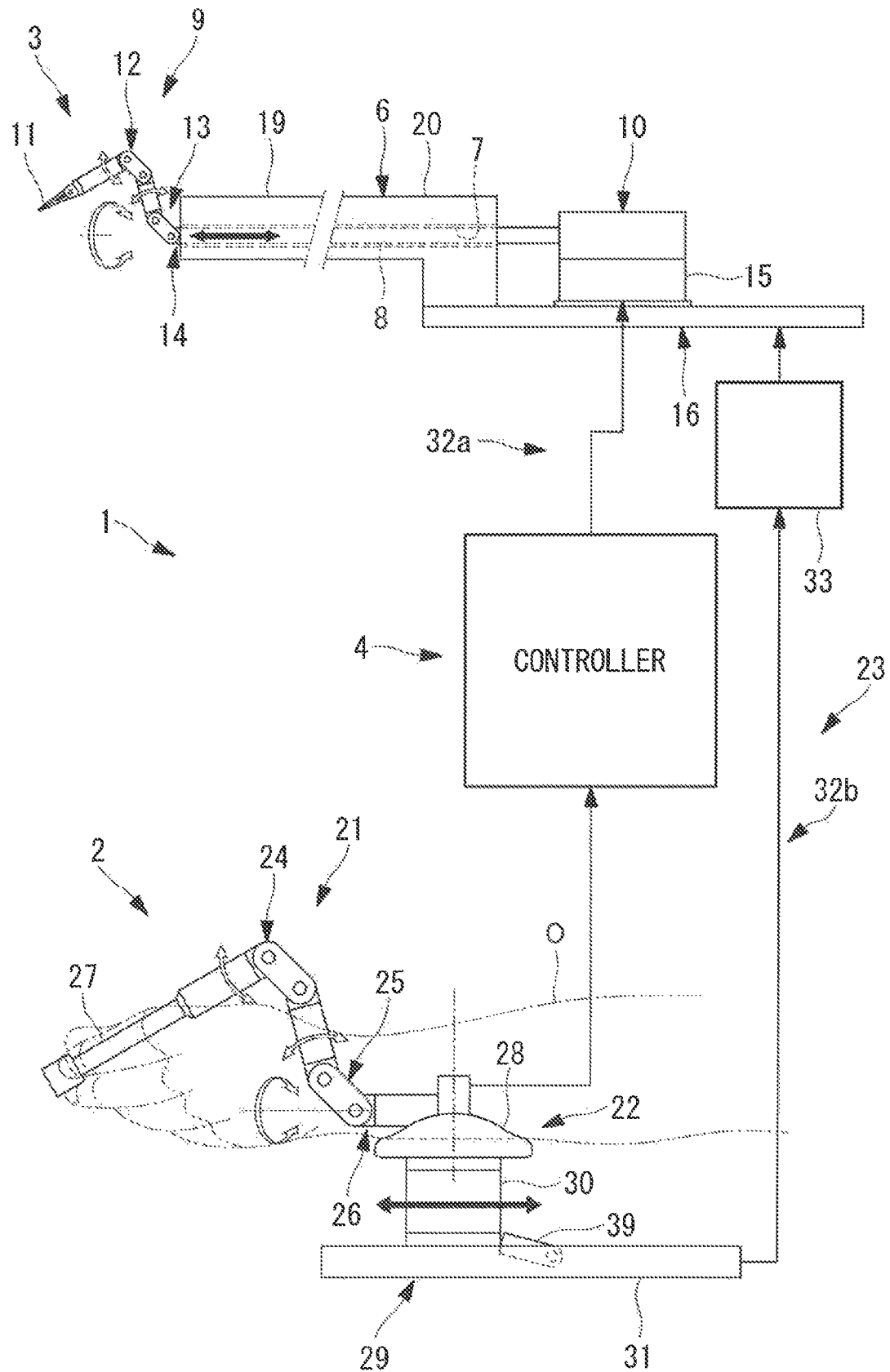
FIG. 5 is a diagram showing a state in which a slider of the second manipulation portion of the medical manipulator system abuts against a stopper.
Figure 6:
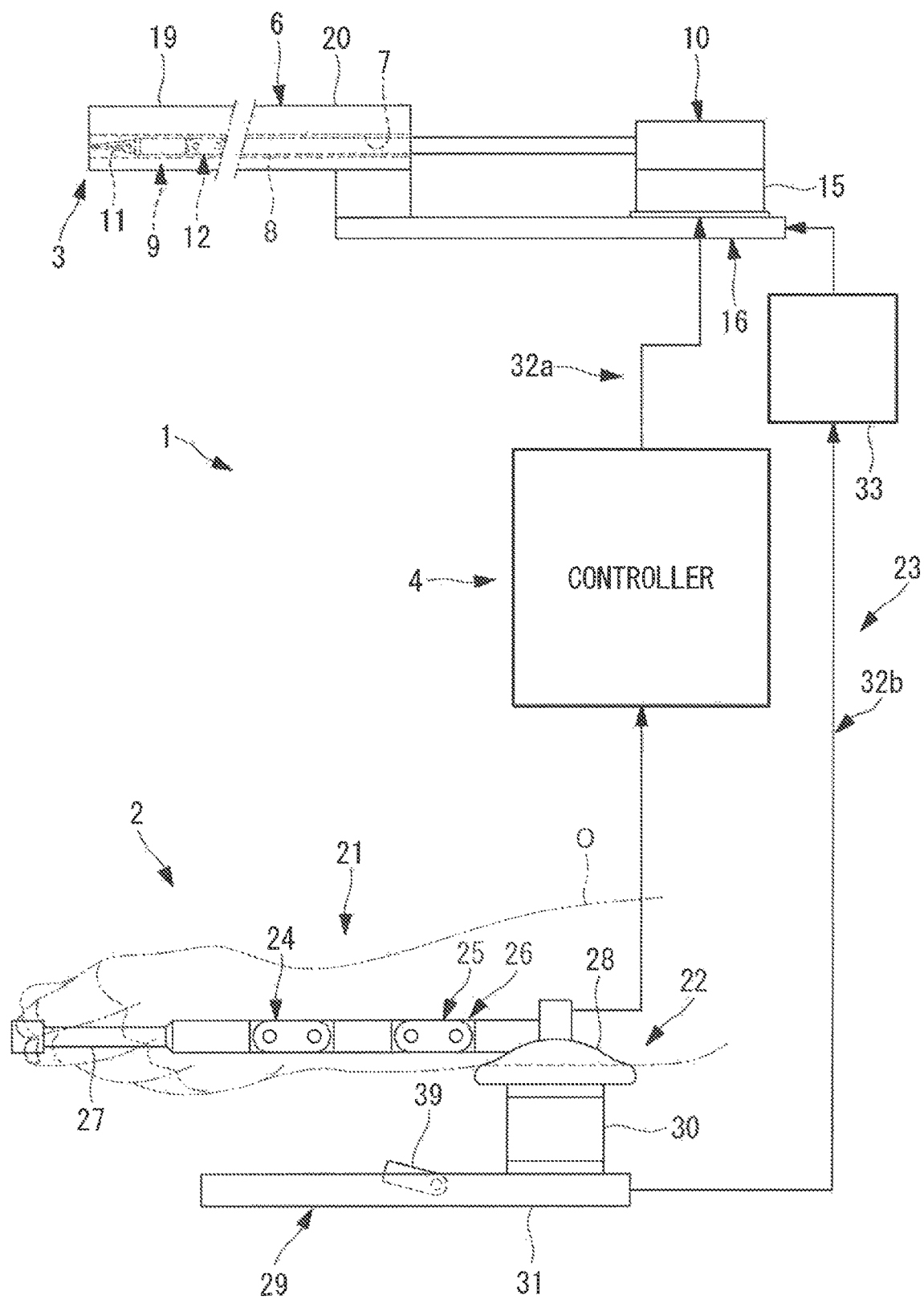
FIG. 6 is a diagram showing an accommodated state in which a movable portion of the medical manipulator system in FIG. 1 is accommodated in a manipulator channel of an overtube.

Thus, as shown in FIGS. 3, 5 and 6, in this embodiment, stoppers (notifying portions) 39 against which the sliders 30 abut in order to restrict further retraction are provided at intermediate positions in the motion ranges of the sliders 30 of the linear motion mechanisms 29. The stoppers 39 are configured so as to abut against the sliders 30 and to restrict further retraction thereof when the joints 14, which are the joints closest to the inserted portions 8 and which compose the movable portions 9, are retracted to positions immediately before the distal end of the overtube 6.

In addition, the stoppers 39 are configured so that the restriction on the retraction of the sliders 30 can be canceled by performing a predetermined manipulation. For example, as shown in FIG. 3, the stoppers 39 are provided so as to be pivotable about the horizontal axes, are biased by springs (not shown) so as to protrude upward, and are configured so as to be pushed down by the sliders 30 when the sliders 30 are moved forward, thus not restricting the movement of the sliders 30 and so as to abut against the rear portions of the sliders 30 when the sliders 30 are retracted, thus restricting the retraction of the sliders 30. Then, in order to cancel the restriction due to the stoppers 39, the stoppers 39 are manipulated so that the stoppers themselves are pushed in the direction orthogonal to the direction in which the sliders 30 are moved, i.e., in this case downward, against the biasing forces of the springs, thus canceling the restriction, so that the sliders 30 are allowed to be retracted.

The operation of the thus-configured medical manipulator system 1 according to this embodiment will be described below.

In order to treat an affected site in the body of the patient P by using the medical manipulator system 1 according to this embodiment, the overtube 6 is inserted into the body cavity of the patient P, and the movable portions 9 and the inserted portions 8 of the manipulators 3 are inserted into the body of the patient P via the manipulator channels 7 of the overtube 6. In addition, the inserted portion 8 of the endoscope 17 is inserted via the endoscope channel 18 of the overtube 6.

Then, as shown in FIG. 3, in a state in which the movable portions 9 are protruding from the distal ends of the manipulator channels 7 of the overtube 6 and are disposed close to the affected site in the body cavity, the operator O manipulates the manipulation input portions 2 while checking images acquired by using the endoscope 17 on the monitor 5. To manipulate the manipulation input portions 2, as shown in FIG. 4, the operator O grips, with both hands, the respective distal-end portions 27 of the two first manipulation portions 21, which form a pair, and places the arms of both hands on the respective armrests 28 of the two second manipulation portions 22, which form a pair.

Then, when the operator O applies a force to one of the armrests 28 by using his/her arm, the slider 30 to which the armrest 28 is secured moves in the direction in which the force is applied, and the amount of that straight movement is converted to the rotational angle by the first rack-and-pinion mechanism 34.

The amount of straight movement that has been converted to the rotational angle of the first rack-and-pinion mechanism 34 is transmitted to the second rack-and-pinion mechanism 35 via the pulleys 36 and 37 and the belt 38, and is converted to the amount of straight movement of the advancing/retracting mechanism 16. Because the motor unit 15 is secured to the advancing/retracting mechanism 16, the driving portion 10 connected to the motor unit 15, the inserted portion 8, and the movable portion 9 are moved, as a single unit, along the longitudinal direction of the inserted portion 8. By this configuration, the treatment portion 11 positioned at the distal end of the movable portion 9 is manually moved forward/backward in a rough manner.

When the operator O moves the distal-end portions 27 of the first manipulation portions 21 which he/she is gripping with both hands by means of forces generated by his/her palms or fingers, that amount of movement is detected by the sensors provided in the individual joints 24, 25, and 26, and is transmitted to the controller 4 in the form of electrical signals. In the controller 4, electrical operation instructions for moving the individual joints 12, 13, and 14 of the movable portions 9 are calculated so as to match the angles of the individual joints 24, 25, and 26 detected by the sensors, and the electrical operation instructions are provided to the motors of the motor units 15 connected to the individual joints 12, 13, and 14. By this configuration, the positions of the distal ends of the treatment portions 11 provided at the distal ends of the movable portions 9 are electrically moved in a precise manner so as to follow the instructions given by using the palms or the fingers.

With the medical manipulator system 1 according to this embodiment, the sliders 30 press the stoppers 39 down when shifting from the accommodated state, in which the movable portions 9 are accommodated in the manipulator channels 7 of the overtube 6, to the treatment state, in which the sliders 30 of the second manipulation portions 22 are moved forward and the movable portions 9 protrude from the manipulator channels 7, thus moving the movable portions 9 forward. On the other hand, when shifting from the treatment state to the accommodated state by retracting the sliders 30 of the second manipulation portions 22, as shown in FIG. 5, the sliders 30 abut against the stoppers 39, thus restricting further retraction.

When the sliders 30 abut against the stoppers 39, because the operator O cannot retract the sliders 30 any further, he/she can recognize that the movable portions 9 are shifting from the treatment state to the accommodated state. Therefore, it is possible to prevent the movable portions 9 from being pulled into the manipulator channels 7 in a state in which the operator O is unintentionally retracting the sliders 30 toward an over-pulled position.

In other words, there is an advantage in which it is possible to prevent the distal ends of the movable portions 9 from being moved toward an unintended direction by preventing the joints 12 and 13 of the movable portions 9 from being forcibly pulled into the manipulator channels 7 in a state in which the joints 12 and 13 of the movable portions 9 are not in their straight state, and also in which it is possible to prevent an excessive load that acts to straighten the flexed joints 12 and 13 of the movable portions 9 from being applied to the joints 12 and 13.

Then, when the operator O who wants to make the movable portions 9 shift to the accommodated state, as shown in FIG. 6, after the individual joints 24 and 25 constituting the movable portions 9 are straightened so as to be a shape which extends along the longitudinal direction of the inserted portions 8 by straightening the individual joints 12 and 13 of the first manipulation portions 21, the stoppers 39 are pressed down to cancel the restricted state, and thus, it becomes possible to accommodate the movable portions 9 in the manipulator channels 7 without resistance by retracting the slider 30.

Note that, the medical manipulator system 1 according to this embodiment may be configured so that the positions of the stoppers 39 can be adjusted in the directions in which the positions of the sliders 30 are moved. The motion-scale ratio may be changed between the treatment state and other states, or the positions of the stoppers 39 may be changed in accordance with cases in which, for example, the lengths and pathways of the manipulators 3 are changed.

In addition, instead of the stoppers 39, or in addition to the stoppers 39, sensors that detect the sliders 30 reaching the positions of the stoppers 39 may be provided, and, when the sensors detect that the sliders 30 reach that positions, the operator O may be notified about this detection by means of a sound, display, or the like.

Figure 7:
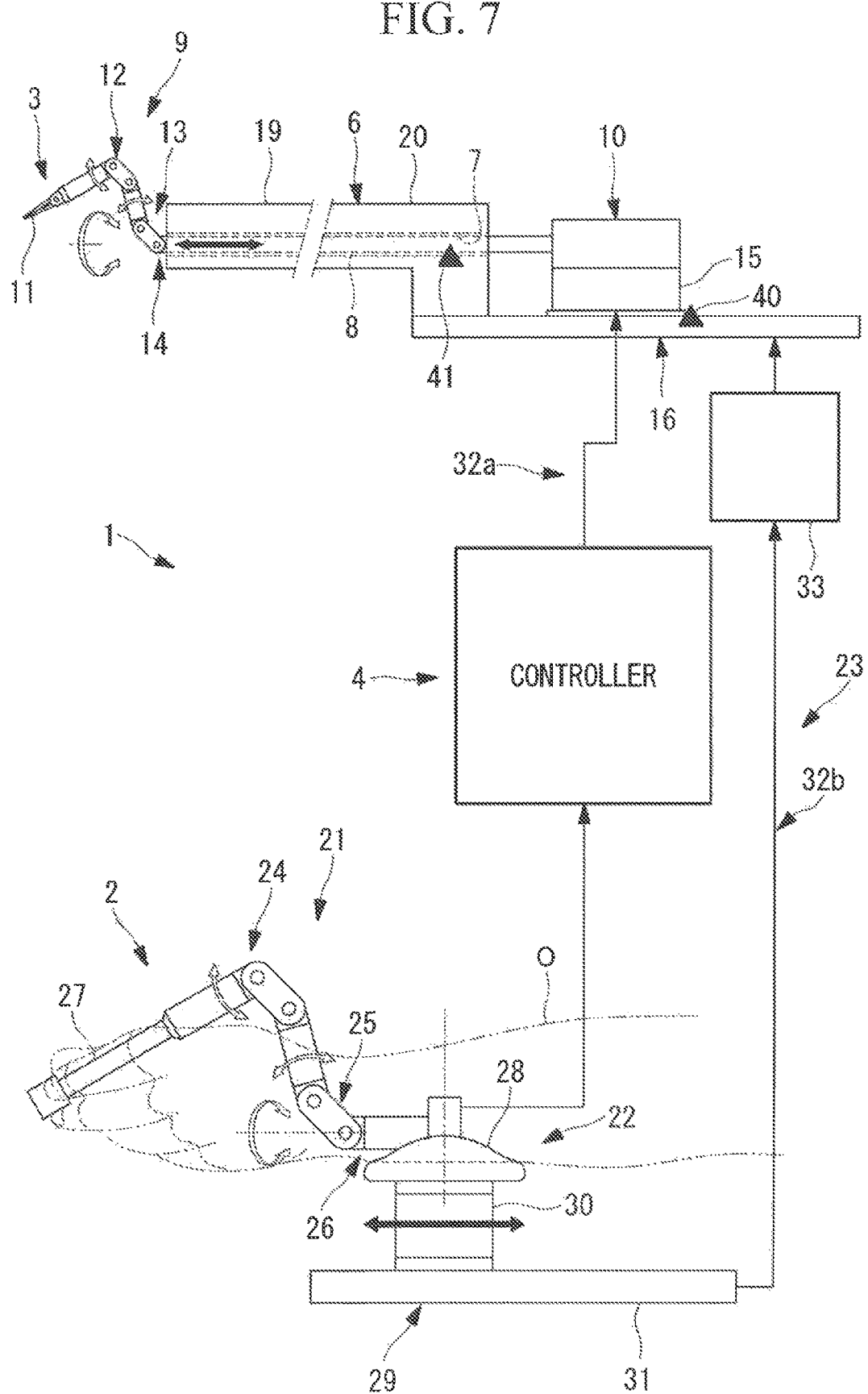
FIG. 7 is a diagram showing another example arrangement of the stopper in the medical manipulator system in FIG. 3.

In addition, in this embodiment, although the stopper 39 against which the slider 30 of the second manipulation portion 22 abut has been described as an example, alternatively, a stopper 40 against which the motor unit 15 abuts, or a stopper 41 against which a depression or a protrusion (not shown) provided in the inserted portion 8 abuts may be provided, as indicated by the filled triangle symbols in FIG. 7. In these cases, it is preferable that a stopper using, for example, an electromagnetic plunger or the like, which can be released in response to instruction signals transmitted thereto from the manipulation input portion 2, is employed as the stopper 40 or 41.

Note that, instead of an electromagnetic plunger, a stopper may be constituted to have a step structure that can be overcome by applying a force thereto.

Figure 8A:
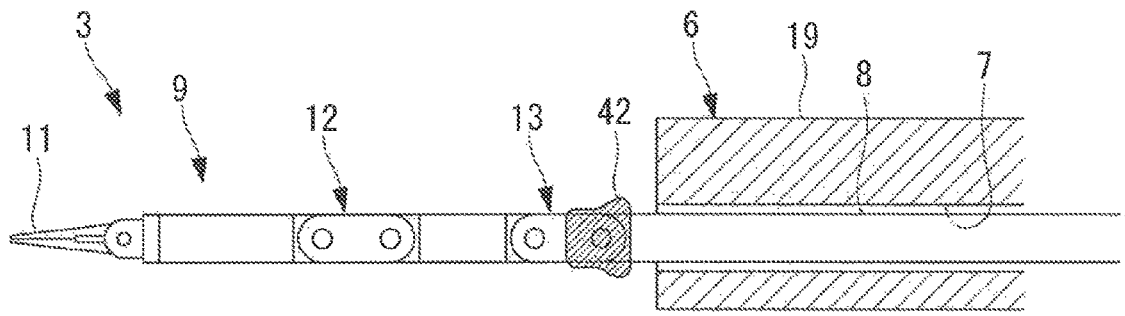
FIG. 8A is a diagram showing a modification of the medical manipulator system in FIG. 1, in which a stopper that is formed of an elastic material and that is attached to the movable portion of the manipulator is provided, and in which the manipulator is placed in a treatment state.
Figure 8B:
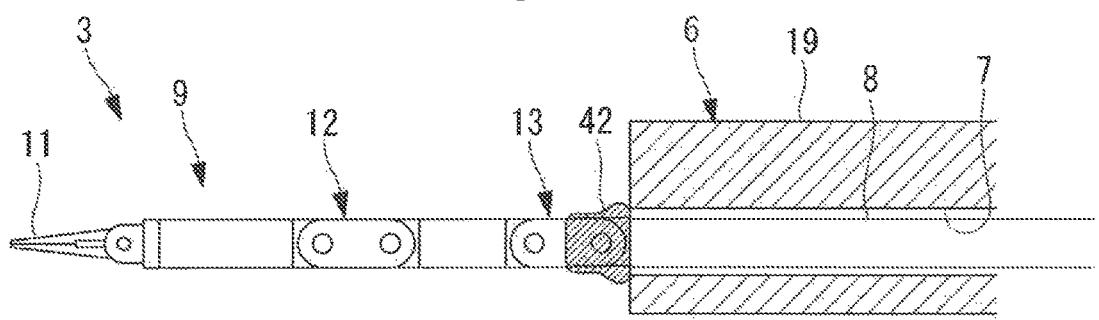
FIG. 8B is a diagram showing a state in which the stopper in FIG. 8A abuts against a distal end of an overtube.
Figure 8C:
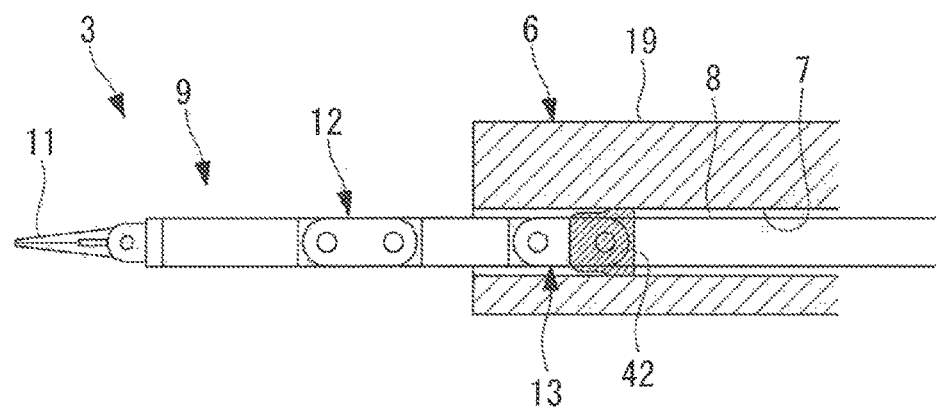
FIG. 8C is a diagram showing a state in which the stopper in FIG. 8A is shrunk in a radial direction, and thus, the manipulator is partially in an accommodated state.

In addition, as shown in FIG. 8A, a stopper 42 formed of a material with which the radial-direction size thereof can be increased/decreased may be provided further on the base-end side than the joint 13 at the most base end of the movable portion 9. The material of the stopper 42 may be formed of, for example, an elastic material, such as a silicone resin or the like. As shown in FIG. 8C, it is possible to make the movable portion 9 pass through the manipulator channel 7 of the overtube 6 when the radial-direction size of the stopper 42 is decreased, and, as shown in FIG. 8B, it is possible to make it difficult for the movable portion 9 to be pulled into the manipulator channel 7 when the radial-direction size of the stopper 42 is increased after reaching outside the distal end of the manipulator channel 7.

Figure 9:
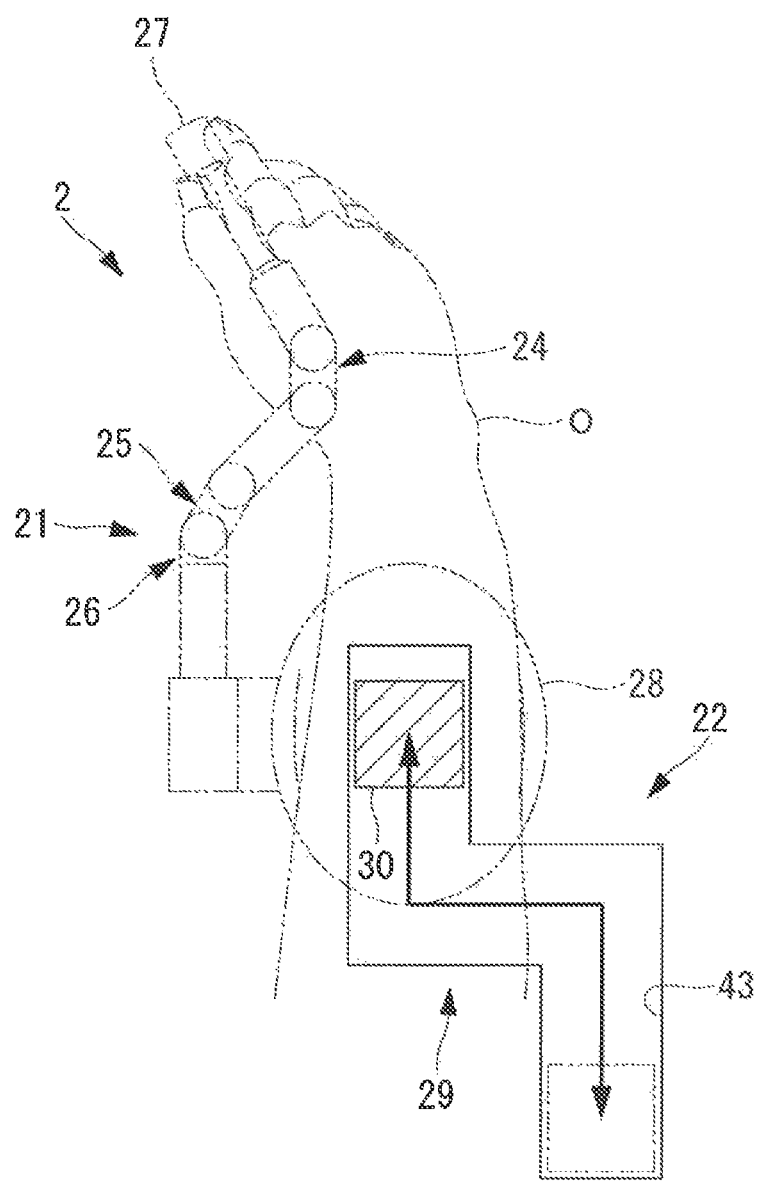
FIG. 9 is a diagram of a modification of the stopper in FIG. 5, showing a case in which the slider of the second manipulation portion moves along a crank-like path.

In addition, as shown in FIG. 9, the slider 30 of the second manipulation portion 22 may be configured so as to be movable in a crank-like manner, and the shift from the treatment state to the accommodated state may be notified to the operator O by retracting the slider 30 so as to abut against a portion of a crank 43 having a step structure. When the operator O intentionally shifts to the accommodated state, by moving the slider 30 by a predetermined distance in a direction perpendicular to the advancing/retracting direction, it is possible to further retract the slider 30 in accordance with the crank 43.

In addition, in this embodiment, the controller 4 may be configured so as to monitor the state of the movable portions 9, to judge whether or not the movable portions 9 are in states in which withdrawal thereof from the treatment state is possible, and to cancel the restriction due to the stoppers 39 when it is judged that the movable portions 9 are in the states in which withdrawal thereof from the treatment state is possible.

Specifically, the controller 4 may judge, on the basis of the angle information detected by the sensors provided in the individual joints 24 and 25 of the first manipulation portions 21, that the movable portions 9 are in the states in which withdrawal thereof from the treatment state is possible when the individual joints 12 and 13 of the manipulators 3 are straight, in other words, when the movable portions have forms in which the inserted portions 8 are extended straight in the longitudinal directions thereof, as shown in FIG. 6.

It suffices that the stoppers 39 be electrical solenoid-driven stoppers or the like with which it is possible to switch between the set state and the released state on the basis of instruction signals transmitted thereto from the controller 4. Alternatively, one-way clutches (cam clutches) that apply restriction in the direction in which the movable portions 9 are pulled into the manipulator channels 7 may be employed.

With the thus-configured medical manipulator system 1 according to this embodiment, the stoppers 39 restrict the movable portions 9 from being pulled into the manipulator channels 7 in the case in which the joints 12 and 13 of the movable portions 9 are flexed, whereas, in the case in which the joints 12 and 13 of the movable portions 9 are straight, the restrictions due to the stoppers 39 are canceled, and thus, there is an advantage in which it is possible to naturally pull the movable portions 9 into the manipulator channels 7.

Specifically, in the case in which the joints 12 and 13 of the movable portions 9 are flexed, by abutting the sliders 30 against the stoppers 39, it is possible to notify the operator O about the fact that an unintended shift from the treatment state to the accommodated state is occurring. On the other hand, in the case in which the joints 12 and 13 of the movable portions 9 are straight, it is possible to shift to the accommodated state without making the operator O aware of the fact that the shift from the treatment state to the accommodated state is occurring.

Figure 10:
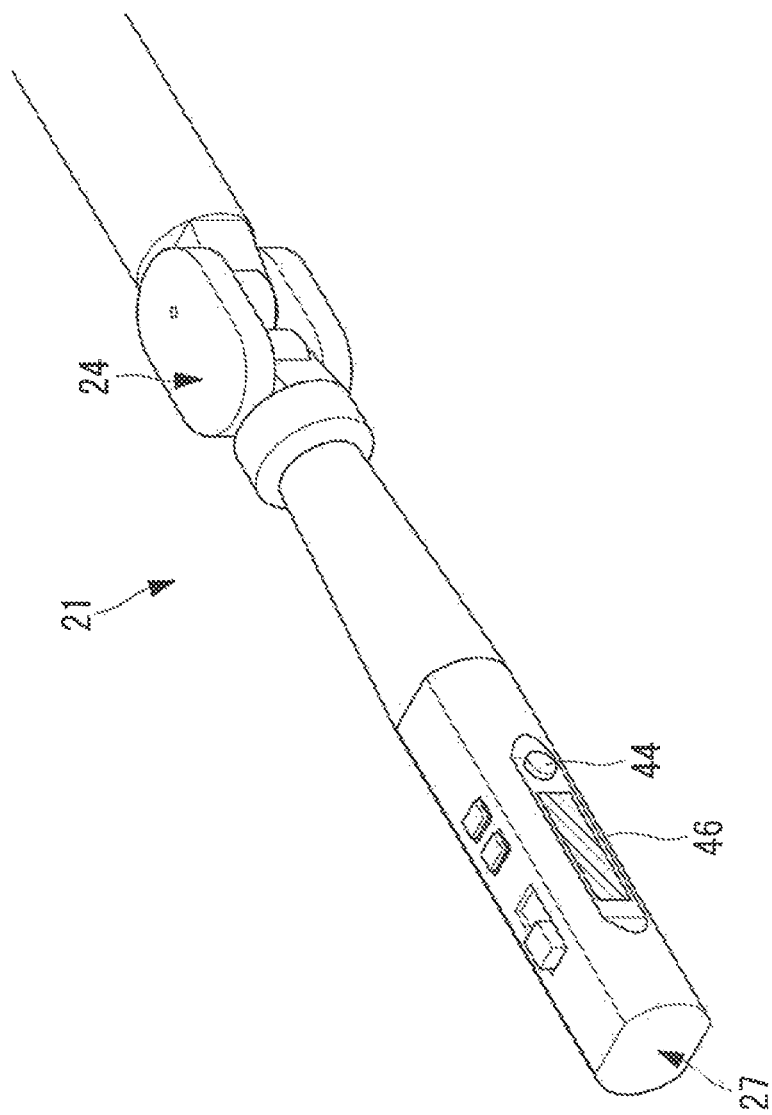
FIG. 10 shows a modification of the medical manipulator system in FIG. 1, and is a perspective view showing examples of a cancelling switch and a contact switch provided in the first manipulation portion.

In addition, in this embodiment, as shown in FIG. 10, cancel buttons (request input portions) 44, with which withdrawal from the treatment state is requested, may be provided at the distal-end portions 27 of the first manipulation portions 21, and, when the cancel buttons 44 are pressed, the controller 4 may perform control so as to release the stoppers 39 and so as to relax the individual joints 12 and 13 of the movable portions 9 by means of the driving portions 10. When the individual joints 12 and 13 of the movable portions 9 are relaxed, because the individual joints 12 and 13 of the movable portions 9 are sequentially straightened when being pulled into the manipulator channels 7, it is possible to prevent unnatural forces from being applied on the joints 12 and 13 and to prevent the treatment portions 11 at the distal ends of the movable portions 9 from being moved in unintended directions.

Note that, in addition to the cancel buttons 44 provided in the distal-end portions 27 of the first manipulation portions 21, contact sensors (dead man's switches) 46 that detect gripping of the first manipulation portions 21 by the operator O may be employed as the request input portions 44, as indicated by hatching in FIG. 10. Because the fact that manipulation is not being performed is detected when the case in which the contact sensors 46 are not detecting the operator O, the individual joints 12 and 13 are relaxed, and thus, it is possible to naturally pull the movable portions 9 into the manipulator channels 7.

In addition, cancel buttons (not shown) provide in the vicinity of the motor unit 15 to which the driving portions 10 of the manipulators 3 are attached may be employed as the request input portions 44. In this case, the stoppers 39 may be disposed at positions at which the stoppers 39 abut against the motor unit 15 or positions at which the stoppers 39 abut against depressions or protrusions provided in the inserted portions 8 in the overtube 6. By pressing the cancel buttons, the restrictions due to the stoppers 39 are canceled, the individual joints 12 and 13 of the movable portions 9 of the manipulators 3 are relaxed, and it becomes also possible to manually move the motor unit 15 attached to the advancing/retracting mechanism 16.

By doing so, not only the operator O but also an assistant can naturally pull the movable portions 9 into the manipulator channels 7 by pressing the cancel buttons.

In addition, in this embodiment, instead of the stoppers 39, sensors (notifying portions) 45 that detect withdrawal from the treatment state are provided in the sliders 30 of the second manipulation portions 22, and, when the sensors 45 detect the withdrawal from the treatment state, a notification about this detection may be issued, and the individual joints 12 and 13 of the movable portions 9 may also be relaxed.

Figure 11:
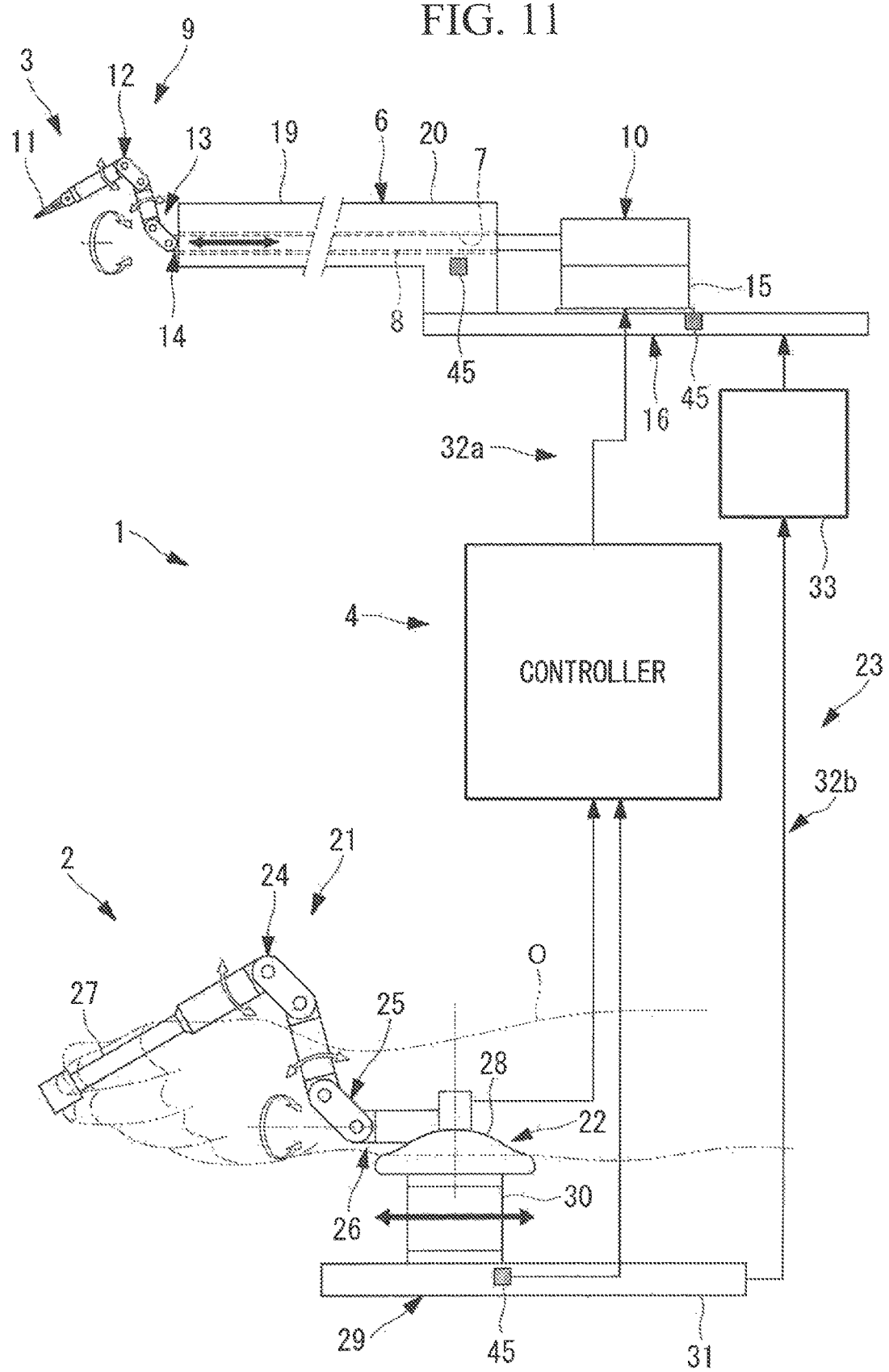
FIG. 11 is a diagram of a modification of the medical manipulator system in FIG. 5, showing an example arrangement of a sensor substituted for the stopper.

As indicated by the hatched rectangles in FIG. 11, the sensors 45 may detect the positions of the sliders 30 of the second manipulation portions 22, or the sensors 45 may detect the position of the motor unit 15 or indicators (not shown) attached to outer surfaces of the inserted portions 8 in the overtube 6.

In addition, in this embodiment, although the advancing/retracting mechanism 16 is moved by the mechanical-driving-power transmitting portion 32b by means of the forces applied to the second manipulation portions 22, alternatively, the advancing/retracting mechanism 16 may electrically be moved by an amount of movement corresponding to the amount by which the sliders 30 of the second manipulation portions 22 are moved.

In this case, at the positions of the stoppers 39 in FIG. 5, switches that are pressed by the rear ends of the sliders 30 of the second manipulation portions 22 may be provided instead of the stoppers 39, and, when the switches are pressed by the sliders 30, the controller 4 may relax the individual joints 12 and 13 of the movable portions 9 and may also move the advancing/retracting mechanism 16 so that the manipulators 3 are retracted by predetermined distances by using the duration during which the switches are pressed as the speed input.

In addition, in this embodiment, although the overtube 6 has been described as an example of a medical device having the channels 7, alternatively, an arbitrary medical device, such as an endoscope or the like may be employed.

In addition, although a case in which the first manipulation portion 21 has a shape that is similar to that of the movable portion 9 of the manipulator 3 has been described as an example, a first manipulation portion 21 having non-similar shape may be employed.

The inventors have arrived at the following aspects of the invention.

An aspect of the present invention is a medical manipulator system including: a manipulator that is provided with an elongated portion, a movable portion which has one or more joints and which is disposed at a distal end of the elongated portion, and a driving portion which is disposed at a proximal end of the elongated portion and which drives the movable portion; a medical device having a channel that can accommodate at least a portion of the elongated portion and the movable portion so as to be movable in a longitudinal direction; a manipulation input portion that generates an operation instruction for moving the manipulator in a longitudinal direction of the elongated portion between a treatment state in which the movable portion completely protrudes from a distal end of the channel and an accommodated state in which the movable portion is accommodated in the channel in accordance with a manipulation instruction input by an operator; and a notifying portion that notifies a situation in which the movable portion is shifting from the treatment state to the accommodated state.

With this aspect, the manipulator is moved in the longitudinal direction of the elongated portion relative to the medical device on the basis of the operation instruction generated in accordance with the manipulation instruction input by the operator via the manipulation input portion. In the treatment state in which the movable portion completely protrudes from the distal end of the channel of the medical device, it is possible to perform treatment by moving the individual joints of the movable portion. On the other hand, when the movable portion, which is in the treatment state, is pulled into the channel of the medical device, the notifying portion notifies the situation in which the manipulator is shifting from the treatment state to the accommodated state. By this configuration, it is possible to prevent the operator from unintentionally pulling the movable portion into the channel. As a result, it is possible to prevent unintended movement of the manipulator caused by forcibly pulling the movable portion into the channel, and it is also possible to reduce the load applied on the joints.

In the above-described aspect, the notifying portion may be a stopper which is provided between the manipulator and the medical device or provided in the manipulation input portion, and which restricts the manipulator from being changed from the treatment state with a manner in which the restriction can be canceled.

With this configuration, when the manipulator is moved in the longitudinal direction of the elongated portion relative to the medical device on the basis of the operation instruction generated in accordance with the manipulation instruction input by the operator via the manipulation input portion, thus shifting from the treatment state to the accommodated state, the state change from the treatment state is restricted by the stopper. In other words, by restricting the state change from the treatment state with the stopper, the operator is notified about the situation in which the movable portion is being shifted from the treatment state to the accommodated state. By this configuration, it is possible to prevent the operator from unintentionally pulling the movable portion into the channel.

In addition, in the above-described aspect, the notifying portion may include a sensor which is provided between the manipulator and the medical device or provided in the manipulation input portion, and which detects the state change of the manipulator from the treatment state, wherein the medical manipulator system is configured to notify the state change when the state change is detected by the sensor.

With this configuration, by detecting the state change with the sensor and by notifying the detection with the notifying portion, the operator can recognize that the state change is taking place, and it is possible to prevent the operator from unintentionally pulling the movable portion into the channel.

In addition, the above-described aspect may be provided with a controller which judges whether or not the manipulator is in a state in which the manipulator can be shifted from the treatment state, and which cancels the restriction by the stopper when the controller judges that the manipulator can be shifted from the treatment state.

By this configuration, the controller monitors the state of the manipulator, judges whether or not the manipulator is in a state in which the manipulator can be shifted from the treatment state, and cancels the restriction by the stopper when the controller judges that the manipulator can be withdrawn from the treatment state. Because the restriction of the stopper is not cancelled when the controller judges that the manipulator is not in a state in which the manipulator can be shifted from the treatment state, it is possible to prevent the operator from unintentionally pulling the movable portion into the channel.

In addition, in the above-described aspect, the controller may judge that the manipulator is in a state in which the manipulator can be shifted from the treatment state when the movable portion extends along the longitudinal direction of the elongated portion.

By this configuration, because the movable portion is smoothly accommodated in the channel when the operator pulls the movable portion into the channel, it is possible to prevent unintentional movement of the joints, and it is possible to reduce the load applied on the joints.

In addition, the above-described aspect may be provided with a request input portion with which a request for shift from the treatment state is input, and a controller which controls the driving portion so as to relax the joints of the movable portion when the request for shift from the treatment state is input via the request input portion.

By this configuration, because the joints of the movable portion are relaxed by the driving portion when the shift request is input via the request input portion, when the operator pulls the movable portion into the channel, the individual joints of the movable portion are pivoted so that the movable portion becomes a shape that extends along the longitudinal direction of the elongated portion and is smoothly accommodated in the channel. By doing so, it is possible to prevent the joints from unintentionally being moved, and it is possible to reduce the load applied on the joints.

In addition, the above-described aspect may be provided with a controller which controls the driving portion so as to relax the joints of the movable portion when the sensor detects the state change.

By this configuration, because the joints of the movable portion are relaxed by the driving portion when the state change is detected by the sensor, when the operator pulls the movable portion into the channel, the individual joints of the movable portion are pivoted so that the movable portion becomes a shape that extends along the longitudinal direction of the elongated portion and is smoothly accommodated in the channel. By doing so, it is possible to prevent the joints from unintentionally being moved, and it is possible to reduce the load applied on the joints.

ADVANTAGEOUS EFFECTS OF INVENTION

The aforementioned aspects afford an advantage in which it is possible to prevent an unintended movement of a manipulator, and it is also possible to reduce the load applied on a joint.

REFERENCE SIGNS LIST 1 medical manipulator system
2 manipulation input portion
3 manipulator
4 controller
6 overtube (medical device)
7 channel
8 inserted portion (elongated portion)
9 movable portion
10 driving portion
39 stopper (notifying portion)
44 cancel button (request input portion)
45 sensor (notifying portion)
46 contact sensor (dead man's switch)

The invention claimed is:

1. A medical manipulator system comprising:
a manipulator that is provided with an elongated portion, a movable portion which has one or more joints and which is disposed at a distal end of the elongated portion, and a motor which is disposed at a proximal end of the elongated portion and which drives the movable portion;
a medical device having a channel that can accommodate at least a portion of the elongated portion and the movable portion so as to be movable in a longitudinal direction;
a manipulation input that generates an operation instruction for moving the manipulator in a longitudinal direction of the elongated portion between a treatment state in which the movable portion completely protrudes from a distal end of the channel and an accommodated state in which the movable portion is accommodated in the channel in accordance with a manipulation instruction input by an operator;
a notifying portion affixed to a linear motion mechanism, the notifying portion comprising a stopper, the notifying portion being configured to provide a notification to an operator when the movable portion shifts from the treatment state to the accommodated state,
wherein the manipulator further comprises a moving portion that is connected to the elongated portion to move the elongated portion and the movable portion in the longitudinal direction,
wherein the manipulation input further comprises a slider that generates the operation instruction for moving the manipulator in the longitudinal direction, and
wherein the stopper is configured to come into contact with the slider, the moving portion, the elongated portion or the medical device to stop the elongated portion and the movable portion from further moving toward a proximal end side of the elongated portion.

2. The medical manipulator system according to claim 1, wherein the stopper is provided between the manipulator and the medical device or provided in the manipulation input, and which restricts the manipulator from being changed from the treatment state with a manner in which the restriction can be canceled.

3. The medical manipulator system according to claim 1, wherein the notifying portion further comprises a, the sensor provided between the manipulator and the medical device or provided in the manipulation input, the notification provided to the operator on a display and/or by production of a sound.

4. The medical manipulator system according to claim 1, further comprising a controller which judges whether or not the manipulator is in a state in which the manipulator can be shifted from the treatment state on the basis of angle information detected by angle sensors provided in the individual joints of the movable portion.

5. The medical manipulator system according to claim 4, wherein the controller is configured to determine, based on the output from the angle sensors, that the manipulator is in a state in which the manipulator can be shifted from the treatment state when, the movable portion extends along the longitudinal direction of the elongated portion.

6. The medical manipulator system according to claim 1, further comprising:
a request input with which a request for shift from the treatment state is input; and
a controller which controls the motor so as to relax the joints of the movable portion when the request for shift from the treatment state is input via the request input portion.

7. The medical manipulator system according to claim 3, further comprising a controller, the controller configured to control the driving portion so as to relax the joints of the movable portion when the sensor detects the state change.

8. A medical manipulator system comprising:
a manipulator that is provided with an elongated portion, a movable portion which has one or more joints and which is disposed at a distal end of the elongated portion, and a motor which is disposed at a proximal end of the elongated portion and which drives the movable portion;

a medical device having a channel that can accommodate at least a portion of the elongated portion and the movable portion so as to be movable in a longitudinal direction;

a manipulation input that generates an operation instruction for moving the manipulator in a longitudinal direction of the elongated portion between a treatment state in which the movable portion completely protrudes from a distal end of the channel and an accommodated state in which the movable portion is accommodated in the channel in accordance with a manipulation instruction input by an operator; and a notifying portion, wherein the manipulation input further comprises a slider and a crank as the notifying portion, the crank configured into a step-shape structure to guide the slider, the slider configured to abut the crank when the movable portion of the manipulator moves toward the medical device and reaches a predetermined position where the movable portion is about to be inserted into the medical device.

* * * * *